United States Patent [19]

Fischer

[11] Plant 4,963

[45] Dec. 7, 1982

[54] AFRICAN VIOLET NAMED PATRICIA

[75] Inventor: Arnold W. Fischer, Hanover, Fed. Rep. of Germany

[73] Assignee: Pan-American Plant Company, Parrish, Fla.

[21] Appl. No.: 252,616

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet plant characterized by its vigorous growth habit and profuse production of dark blue flowers of excellent substance and of single to semi-double form. The flower corolla is rotate and sympetalous and the flower has an excellent keeping quality.

3 Drawing Figures

BACKGROUND OF THE NEW PLANT

This new African violet plant originated as a seedling of unknown parentage growing among breeding stock maintained by me at Hanover, West Germany, for the production of new violet varieties of commercial merit. This plant was discovered by me in my greenhouse at Hanover and was selected for propagation and test because of its vigorous growth and profuse production of flowers. I reproduced the discovery plant, by means of cuttings, at Hanover with favorable results and subsequently propagated the plant through successive generations, which demonstrated that the novel characteristics of the plant would hold true from generation to generation and appeared to be firmly fixed. This new African Violet plant is now being propagated on a commercial scale, by means of cuttings, at West Chicago, Ill., and at Parrish, Fla.

DESCRIPTION OF THE DRAWINGS

This new violet plant is illustrated by the accompanying drawings, of which sheet 1 is a full color photographic view of a potted plant in full bloom, and sheets 2 and 4 are prints of machine copies of the front and back sides, respectively, of typical leaves of this plant.

DESCRIPTION OF THE NEW PLANT

The following is a detailed description of the new plant based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African Violet.

Form: Compact and of rosette shape.
Growth: Vigorous and strong.
Growth rate: Rapid.
Foliage:
- *Quantity.*—Moderate, with about 17 leaves.
- *Size of leaf.*—Length — From insignificant to about 95 mm. Width — From insignificant to about 85 mm.

- *Shape of leaf.*—Ovate with rounded apex and repand margins.
- *Texture.*—Pubescent.
- *Color.*—Upper Side — 137A. Under Side — 138D.
- *Ribs and veins.*—Pinnate.
- *Leaflets.*—None.
- *Petioles.*—Length — From insignificant to about 90 mm.

THE BUD

Form: Globular.
Size: Average, with various lengths and diameters at time of opening.
Shape: Vase-shaped.
Opening rate: Typical violet.
Color of petals:
- *When sepals first divide.*—87B.
- *When petals begin to unfurl.*—89A.

Sepals:
- *Number.*—Five.
- *Shape.*—Lanceolate and branched becoming flat when flowers open.
- *Color.*—Inside — 148B. Outside — 148B.
- *Striae.*—None.

Calyx:
- *Size.*—Small.
- *Shape.*—Calyx splits to star shape.

Penduncle:
- *Character.*—Rigid and erect.
- *Aspect.*—Hairy.

THE FLOWER

Blooming habit: Intermittent.
Flowering: Profusely.
Flower size: Large.
- *Diameter.*—About 30 to 40 mm.
- *Borne.*—As a cyme.
- *Shape.*—When bloom first opens, cup-shaped; becoming flat as the bloom matures.

Petalage:
- *Numer of petals.*—Five.
- *Arrangement.*—Sympetalous.
- *Form.*—Rotate — zygomorphic with repand margin.
- *Texture.*—Soft.
- *Appearance.*—Satiny.
- *Color.*—Upper Side — 89A. Under Side — 89D.

Petaloids:

*Number.*—From two to four.
*Color.*—Upper Side — 89A. Under Side — 89C.
Flower stem:
*Length.*—From insignificant to about 80 mm.
*Character.*—Strong and upright.
*Color.*—177C.
Persistence: The flowers hang on and dry.
Fragrance: None.
Lasting quality:
*On the plant.*—From 10 to 20 days when fully opened.

REPRODUCTIVE ORGANS

Stamens:
*Anthers.*—Number: Two. Arrangement: Monadelphous. Size: About 3 mm. square. Color: Yellow.
*Filaments.*—Length: About 3 mm. Color: Whitish yellow.
*Pollen.*—Color — Yellow.

Pistils:
*Number.*—One.
*Styles.*—Length: About 5 mm. Color: 89A.
*Stigma.*—Color — Whitish.
Ovaries: Hypogynous and tomentose.

This new variety of African Violet plant is particularly distinguished by its profuse blooms borne as in a bouquet above the medium green foliage of the plant. The flower corolla is rotate and sympetalous with three larger and two smaller petals and the flower is single to semi-double with excellent keeping quality.

I claim:

1. A new African Violet cultivar, substantially as herein shown and described, characterized by its profuse production of large, dark blue flowers of single and semi-double form borne on upright stems to cluster as a bouquet above the plant foliage.

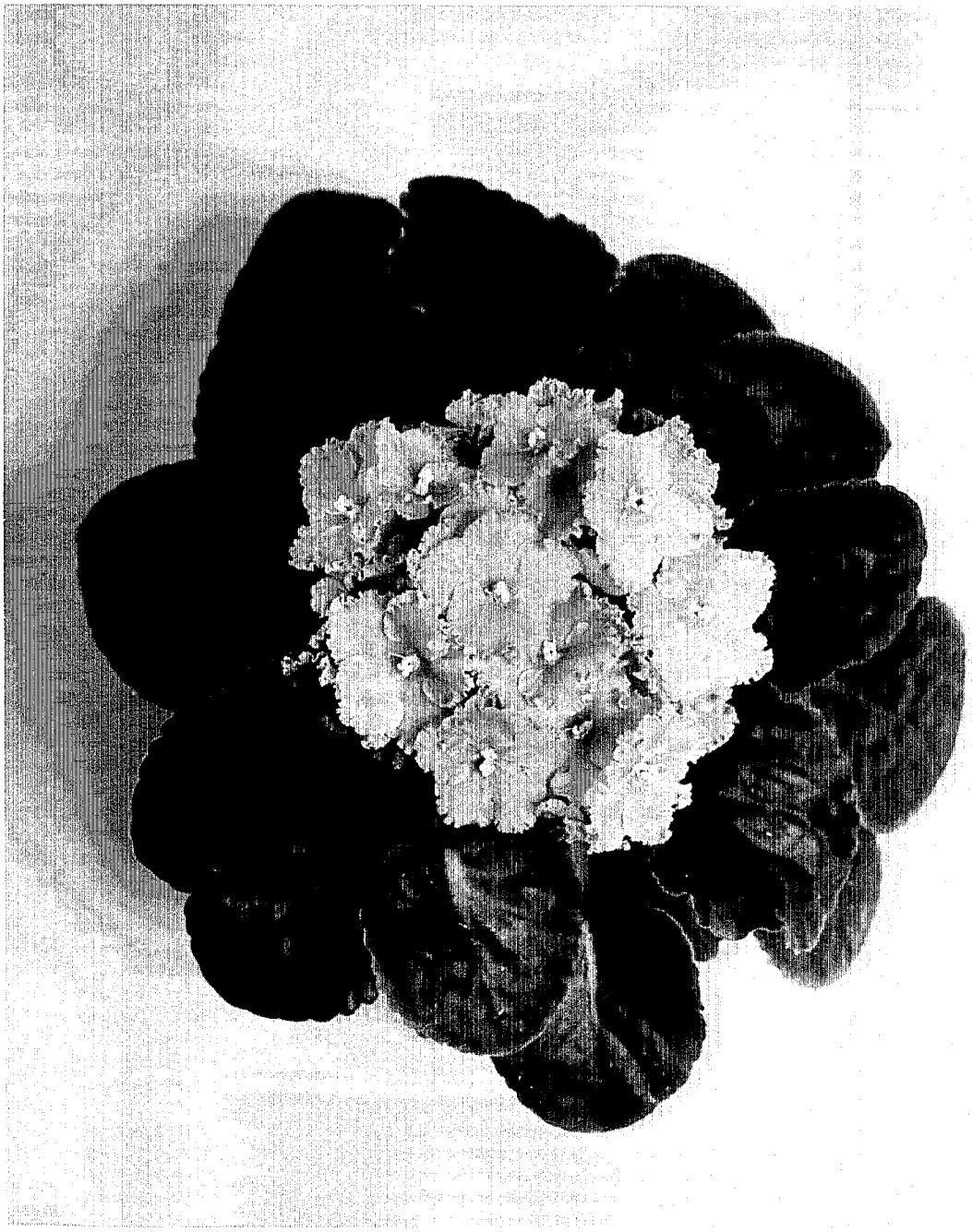

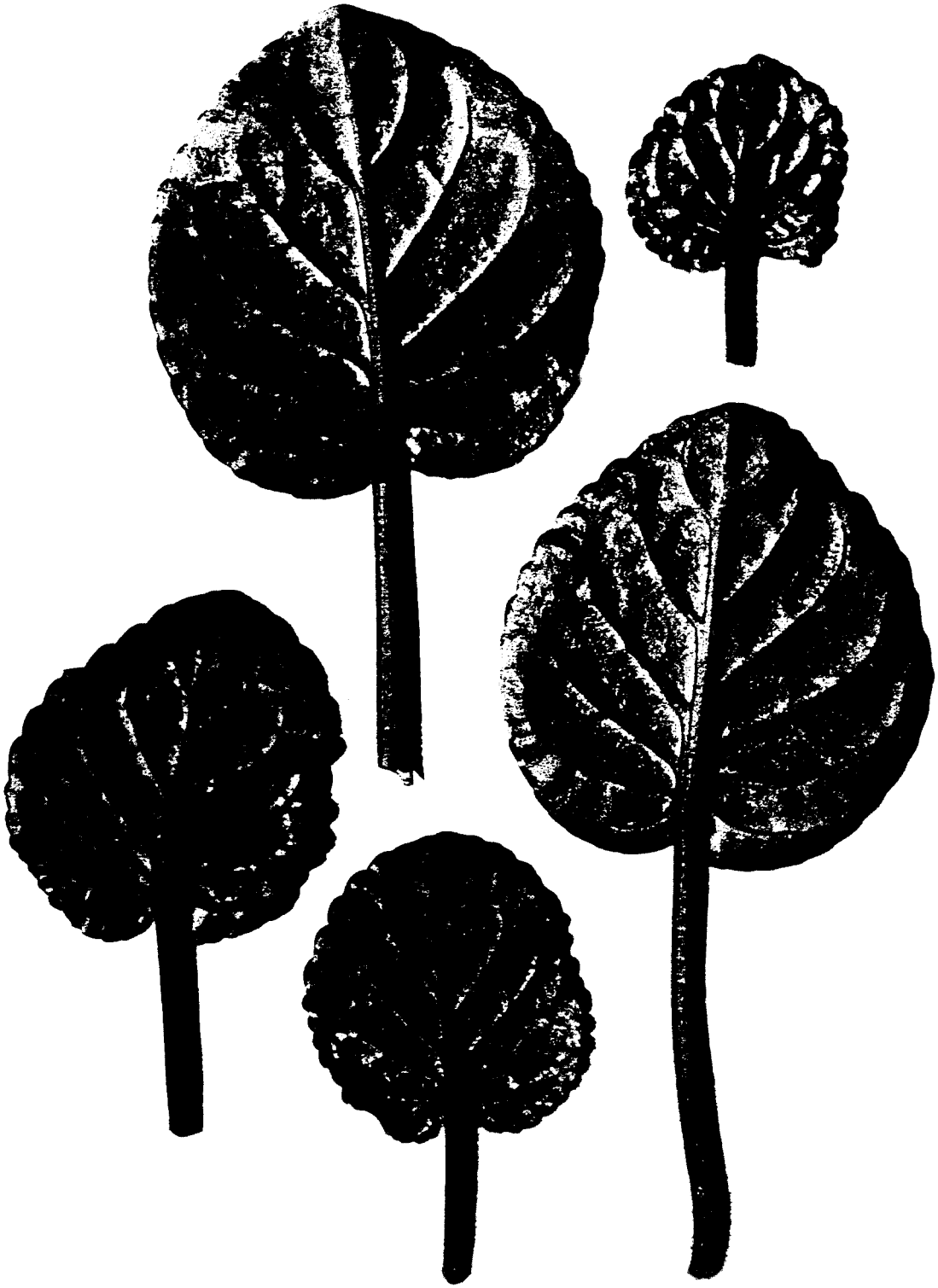

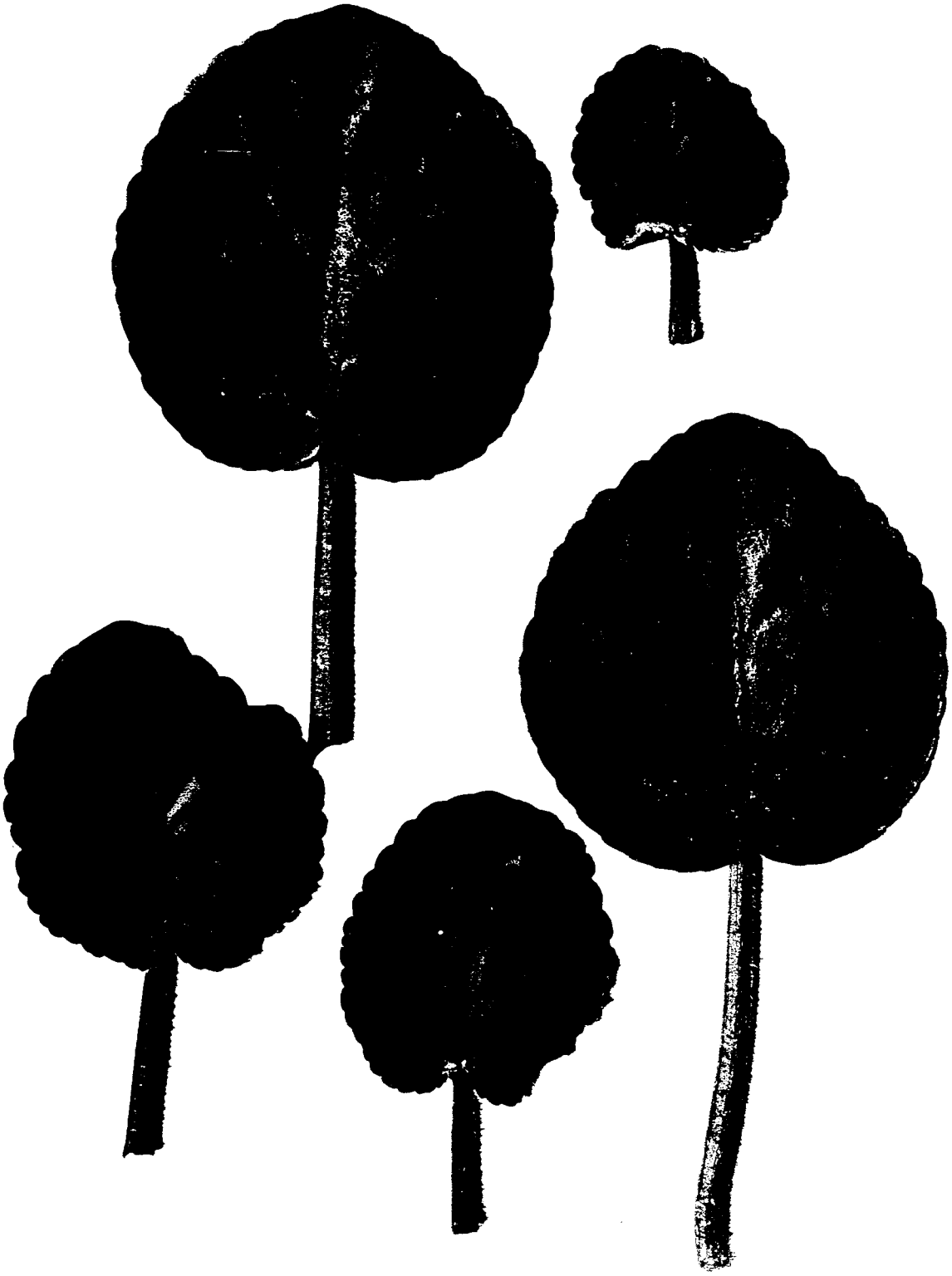

* * * * *